United States Patent
Baik

(10) Patent No.: US 6,178,963 B1
(45) Date of Patent: Jan. 30, 2001

(54) HEAT PACK

(76) Inventor: Chang-Pyoung Baik, 276-18 Wolgae-Dong, Nowon-Gu, Seoul (KR)

( * ) Notice: Under 35 U.S.C. 154(b), the term of this patent shall be extended for 0 days.

(21) Appl. No.: 09/444,345

(22) Filed: Nov. 19, 1999

(51) Int. Cl.[7] ............................................. F24T 1/00
(52) U.S. Cl. ...................... 126/263.03; 126/400
(58) Field of Search .................. 126/263.03, 263.04, 126/400; 422/245.1

(56) References Cited

U.S. PATENT DOCUMENTS

| | | |
|---|---|---|
| 4,829,980 | 5/1989 | Smith . |
| 5,056,589 * | 10/1991 | Hettel et al. ............... 126/263.04 |
| 5,205,278 * | 4/1993 | Wang ............................ 126/263.03 |
| 5,736,110 | 4/1998 | Angelillo et al. . |

* cited by examiner

*Primary Examiner*—Carl D. Price
(74) *Attorney, Agent, or Firm*—Dann, Dorfman, Herrell & Skillman, P.C.; Henry H. Skillman

(57) ABSTRACT

Disclosed is a heat pack A heat pack comprising a flexible container; a solution which is filled in the container and generates a heat while be crystalizing; a trigger which is disposed in the container to be in contact with the solution, for making the solution generate the heat, wherein the trigger is a single coil spring, and the coil spring has windings in close contact with each other or the coil spring has windings which are partially contacted with each other.

6 Claims, 3 Drawing Sheets

HEAT PACK

BACKGROUND OF THE INVENTION

1. Field of the Invention

The present invention relates to a heat pack, and more particularly to a heat pack which is provided with a coil type trigger.

2. Description of the Prior Art

There are provided various kinds of heat packs in accordance with a shape of a trigger which is operated in a supersaturated solution of the heat pack.

As an example of the heat pack, U.S. Pat. No. 5,205,278 discloses a chemical bag warmer comprising a sealed bag which is made of PVC, P.P, P.U. plastic and in which a sodium acetate solution is filled, and a triggering member which is mounted in the sodium acetate and generates an oscillation wave effect in the sodium acetate solution. The triggering member is a disc-shaped member, of which the center portion is a cross-shaped part extended to the edge thereof to divide the center portion into four sectors; each sector has a plurality of fragmental concentric circles to form into a rugged surface, the rugged surface can facilitate the triggering member to bend and vibrate so as to generate the better oscillation wave effect.

Further, U.S. Pat. No. 5,736,110 discloses an activator for initiating crystallization of a supersaturated solution within a flexible container. The activator comprises a flexible screen for immersing in the supersaturated solution within the flexible container. The flexible screen defines a plurality of apertures therein with an activation material being affixed to the screen within the plurality of apertures. Upon flexing of the flexible screen by an operator, the activation material interacts with the screen to initiate crystallization of the supersaturated solution.

In U.S. Pat. No. 4,829,980, there is disclosed a trigger device for a heat pack comprises three helically-coiled, resilient metallic filaments 1,2,3 nested one within the other and of inwardly decreasing diameter, the filament 2 is wound in a sense opposite to that of filaments 1 and 3. Flexing the assembly of nested helices about its longitudinal axes produces a rubbing action between adjacent turns thereof which initiates crystallization. Other devices comprises two nested helices wound in the same sense; a single helix having a pressure plate at one end and an external or internal cap at the other; and a body of randomly convoluted or woven metallic filament.

However, in case of the U.S. Pat. No. 5,205,278 among the constructions of the triggers of the conventional heat packs, as described above, since the triggering member is a flexible metallic piece having the disc-shape, the triggering member may be damaged, when being repeatedly used over a long time. In addition, in case of the flexible screen of the U.S. Pat. No. 5,736,110, such problem may be seriously raised.

Meanwhile, in case of the U.S. Pat. No. 4,829,980, there should be provided a process of nesting a plurality of filaments in order to manufacture the trigger. This makes the manufacturing process complex. Also, in case of the single helix, the single helix has to have a pressure plate at one end and an external or internal cap at the other. Therefore, since there should be provided further process of mounting the pressure plate and cap, there is a difficulty in the manufacturing process.

And in case of the trigger in which two or more filaments are nested, since the plurality of filaments have to be bent in order to crystallize the supersaturated solution, there is a problem that it is too hard for a user to operate the trigger. In case of the single helix having the pressure plate at one end and the external or internal cap at the other, since the user has to apply a big force to the pressure plate and the cap so as to suppress an elastic force of the filament, it is also difficult to operate the trigger.

SUMMARY OF THE INVENTION

The present invention has been made to overcome the above described problem of the prior art.

It is an object of the present invention to provide a heat pack including a trigger which can be prevented from being destroyed in spite of being repeatedly bent, thereby extending a life time thereof.

It is other object of the present invention to provide a heat pack including a trigger of which manufacturing process is simple.

It is another object of the present invention to provide a heat pack including a trigger for making a solution generate a heat, which facilitates gripping and bending.

To accomplish the above object of the present invention, there is provided a heat pack comprising a flexible container; a solution in the container which generates heat while crystallizing; a trigger which is disposed in the container to be in contact with the solution, for making the solution generate the heat, wherein the trigger is a single coil spring, and the coil spring has windings in close contact with each other.

According to the present invention, there is further provided a heat pack comprising a flexible container; a solution in the container which generates a heat while crystallizing; a trigger which is disposed in the container to be in contact with the solution, for making the solution generate the heat, wherein the trigger is a single coil spring, and the coil spring has windings which are partially contacted with each other.

BRIEF DESCRIPTION OF THE DRAWINGS

The above objects and other advantages of the present invention will become more apparent by describing in detail the preferred embodiments thereof with reference to the attached drawings, in which.

DESCRIPTION OF THE PREFERRED EMBODIMENTS

Hereinafter, a heat pack according to an embodiment of the present invention will be described in detail with reference to the accompanying drawings.

Figure 1:
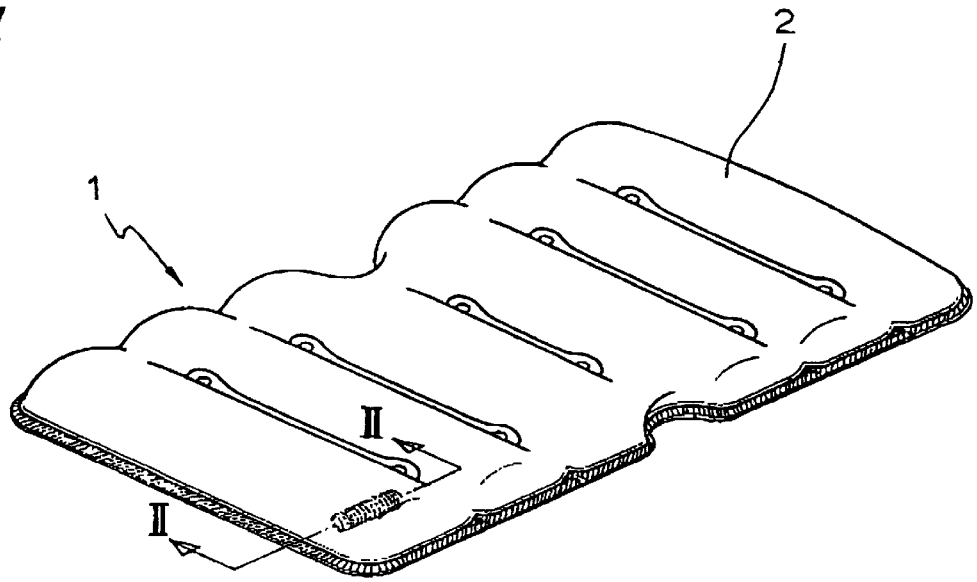
FIG. 1 is a perspective view of a heat pack according to the present invention.
Figure 2:
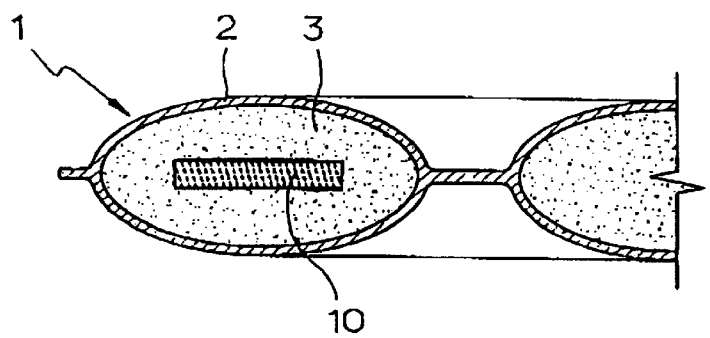
FIG. 2 is a sectional view along line II—II in FIG. 1.
Figure 3:
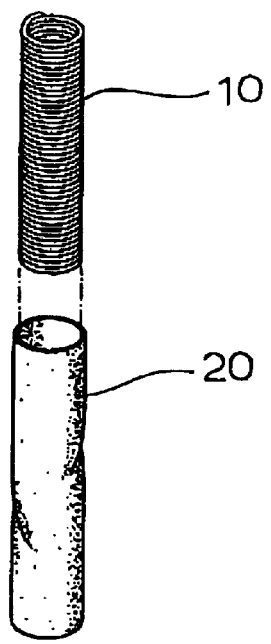
FIG. 3 is a perspective view of a first embodiment of a trigger applied to the heat pack according to the present invention.
Figure 4A:
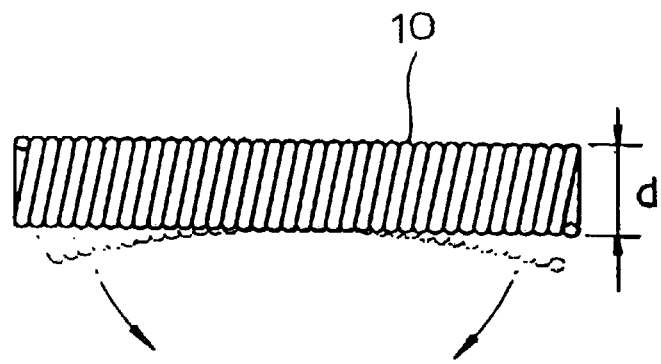
FIGS. 4a and 4b are views showing an operation of the trigger applied to the heat pack according to the first embodiment of the present invention.
Figure 4B:
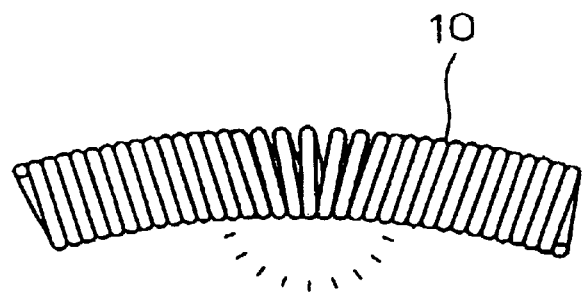

A heat pack according to a first embodiment of the present invention, as shown in FIGS. 1 and 2, comprises a container 2 which is made of a flexible material such as polyethylene, PVC, and so forth, a sodium acetate solution which is supercooled below a solidification point in the container 2 so as not to leak from the container 2, a single coil spring 10 for generating a crystallization reaction of the sodium acetate solution, which is used as a trigger.

The coil spring 10 has windings in close contact with each other so that the spacing between the windings is zero. On the outer face of the coil spring 10, there is provided a tube 20 made of rubber.

Hereinafter, an operation of the heat pack according to the first embodiment of the present invention will be described.

When the coil spring 10 is bent by an user to use the heat pack 1, it causes the windings of the coil spring 10 to make a friction therebetween, resulting in a generation of spark. The spark makes the solution react. The solution is crystalized while the reaction of the solution is widely spread around the coil spring 10.

As the solution 3 starts to generate the heat, the coil spring 10 may be returned by a resilient force to the initial state.

Figure 5:
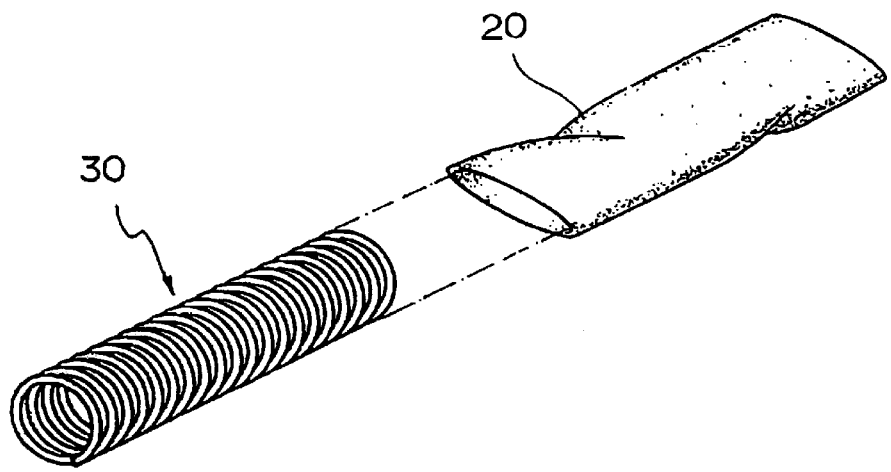
FIG. 5 is a perspective view of a second embodiment of a trigger applied to the heat pack according to the present invention.

In a second embodiment of the trigger according to the present invention, as shown in FIG. 5, a coil spring 30 used as the trigger has windings which are partially contacted with each other.

That is, the coil spring 30 is deformed so that the windings are laid down to one side. Therefore, Since the windings are partially contacted with each other, it is not necessary to limit a pitch between the windings.

The coil spring 30 has a longitudinal axis and a series of interconnected coil windings. Each of the windings is generally circular and is laid down in a plane disposed at an acute angle to the longitudinal axis of the spring. The width of the coil spring along the length of the longitudinal axis is equal to the diameters of the circular windings, and the thickness of the coil spring along the length of the longitudinal axis is less than the diameters of the circular winding.

The coil spring 30 is covered with a tube 20 made of rubber.

The operation of crystallization of the solution is the same as the first embodiment of the trigger according to the present invention.

Figure 6A:
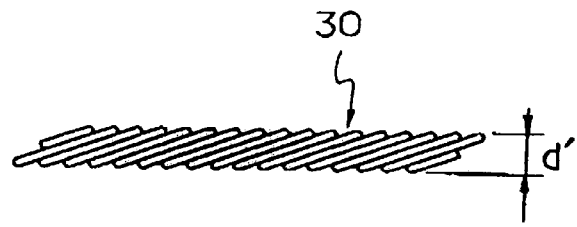
FIGS. 6a and 6b are views showing an operation of the trigger applied to the heat pack according to the second embodiment of the present invention.
Figure 6B:
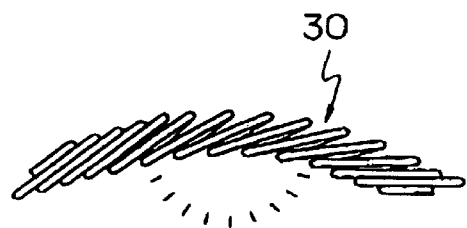

That is, as shown in FIGS. 6a and 6b, When the coil spring 10 is bent by an user to use the heat pack 1, it causes the windings of the coil spring 10 to make a friction therebetween, resulting in a generation of spark. The spark makes the solution react. The solution is crystalized while the reaction of the solution is widely spread around the coil spring 10.

As described as above, since the thickness of the coil spring 30 according the the second embodiment of the present invention is smaller than that of the coil spring 10 of the second embodiment (d>d'), the occupation space of the spring 30 can be reduced.

In addition, since the coil spring 30 is in a state that its windings are laid down to one side, at least two coil spring 30 can be manufactured with one coil spring 10, whereby the manufacturing cost can be lowered.

Further, since the coil spring 30 is not compressed, the bending operation of the coil spring 30 is facilitated giving the user convenience.

According to the present invention, as described above, the coil spring 10, 30 cannot be broken in spite of being bent many times, resulting in extending the life time of the heat pack 1.

In the trigger according to the present invention, it is not necessary to provide a separate manufacturing process.

While the present invention has been particularly shown and described with reference to particular embodiments thereof, it will be understood by those skilled in the art that various changes in form and detail may be effected therein without departing from the scope of the invention as defined by the appended claims.

What is claimed is:

1. A heat pack comprising:
    a flexible container;
    a solution in the container, said solution generating heat while crystalizing;
    a trigger disposed in the container in contact with the solution, for making the solution generate the heat,
    wherein the trigger is a single coil spring, said coil spring having a longitudinal axis and a series of interconnected coil windings laid down to one side so that the windings are partially contacted with each other, each of said windings being generally circular and laid down in a plane disposed at an acute angle to the longitudinal axis of the spring, the width of said coil spring along the length of the longitudinal axis being equal to the diameters of the circular windings, and thickness of the said coil spring along the length of the longitudinal axis being less than the diameters of the circular windings.

2. A heat pack as claimed in claim 1, wherein the container is made of polyethylene or PVC.

3. A heat pack as claimed in claim 1, wherein the solution is a salt solution.

4. A heat pack as claimed in claim 3, wherein the salt solution is a sodium acetate solution.

5. A heat pack as claimed in claim 1, further comprising a cover provided on an outer face of the trigger.

6. A heat pack as claimed in claim 5, wherein the cover is made of rubber.

* * * * *

UNITED STATES PATENT AND TRADEMARK OFFICE
CERTIFICATE OF CORRECTION

PATENT NO. : 6,178,963 B1  Page 1 of 1
DATED : January 30, 2001
INVENTOR(S) : Baik, Chang-Pyoung It is certified that error appears in the above-identified patent and that said Letters Patent is hereby corrected as shown below:

Title page,
Insert the following:

-- [30] Foreign Application Priority Data
     Nov. 19, 1998   [KR]   Korea ..........................22626/1998
     Oct. 26, 1999   [KR]   Korea..........................23087/1999 --

Signed and Sealed this

Twenty-third Day of October, 2001

Attest:

NICHOLAS P. GODICI
*Attesting Officer*  *Acting Director of the United States Patent and Trademark Office*